United States Patent [19]
Soane

[11] Patent Number: 5,135,627
[45] Date of Patent: Aug. 4, 1992

[54] MOSAIC MICROCOLUMNS, SLABS, AND SEPARATION MEDIA FOR ELECTROPHORESIS AND CHROMATOGRAPHY

[75] Inventor: David S. Soane, Piedmont, Calif.

[73] Assignee: Soane Technologies, Inc., Hayward, Calif.

[21] Appl. No.: 597,528

[22] Filed: Oct. 15, 1990

[51] Int. Cl.$^5$ .................. C25B 1/00; B01D 57/02; B01D 61/42
[52] U.S. Cl. .................. 204/182.8; 204/180.1; 204/299 R; 428/327
[58] Field of Search ............. 204/182.8, 180.1, 299 R; 428/327

[56] References Cited

U.S. PATENT DOCUMENTS

| | | | |
|---|---|---|---|
| 3,922,432 | 11/1975 | Renn | 204/182.8 |
| 4,856,706 | 9/1989 | Karger et al. | |
| 4,865,707 | 9/1989 | Karger et al. | |
| 4,883,597 | 11/1989 | Perlman | |
| 4,911,807 | 3/1990 | Burd | |
| 4,963,243 | 10/1990 | Ogawa | 204/182.8 |

OTHER PUBLICATIONS

Brown and Pietrzyk, *J. Chromatography* 466, 291–300 (1989).
Issaq, et al., *J. Liquid Chromatography* 11(2), 333–348 (1988).

*Primary Examiner*—John Niebling
*Assistant Examiner*—Caroline Koestner
*Attorney, Agent, or Firm*—Kilpatrick & Cody

[57] ABSTRACT

A method and compositions for separating molecules based on molecular size, shape, affinity, chirality, weight, charge, and hydrogen bonding, using a mosaic matrix formed by polymerizing a dispersion of dispersoids within a polymeric matrix. The dispersoids and matrix can be of the same or different hydrophobicity or hydrophilicity. The dispersoids can be porous or nonporous. The mosaic matrix can be used with existing chromatographic and electrophoresis apparatus to effect an enhanced separation of molecules, particularly of nucleic acids and peptides, by application of a solution and/or an electrical field to the matrix. The solution can form a pH, ionic, or composition gradient, and be applied using gravity or under pressure. The electrical field can be continuous, pulsed, or two-dimensional.

33 Claims, 1 Drawing Sheet

MOSAIC MICROCOLUMNS, SLABS, AND SEPARATION MEDIA FOR ELECTROPHORESIS AND CHROMATOGRAPHY

BACKGROUND OF THE INVENTION

This invention generally relates to polymeric matrices for combined or individual chromatographic or electrophoretic separations of mixtures, and is in particular a mosaic matrix formed from a combination of hydrophilic or hydrophobic materials uniformly dispersed throughout a crosslinked polymer network.

Separations of biological or synthetic (e.g., pharmaceutical products, organic or inorganic mixtures) materials rely primarily on differences in molecular weight or differences in overall charge of the molecules. These separations commonly fall into two categories, chromatographic separations and electrophoretic separations.

Chromatographic separations usually involve the use of a polymeric packing or coated silica particles in combination with an elution buffer that forces the material to be separated through the matrix, where molecules move at a different rate depending on their affinity toward the packing. In case of polymer packing, the matrix may be formed of a crosslinked polymeric gel or small particles of crosslinked polymer. The porosity of the gel and/or particles effects the separation based on the molecular weight. The polymer may also be charged and separation effected by altering pH and/or ionic concentration, either by batch elutions or by gradient elution. Other specific interactions may also play a role, such as in affinity chromatography, chiral separation, ion-exchange and reverse-phase liquid chromatography.

Materials for use in chromatographic separations have been commercially available for many years, and include agarose and acrylamide gel and cellulose derivative beads such as Sephadex TM and Sepharose TM, manufactured by Pharmacia Chemical Co., Piscataway, N.J., cellulose and hydroxy apatite resins, distributed by Sigma Chemical Co., St. Louis, Mo., and polystyrene crosslinked with divinylbenzene produced by Dow, Midland, Mi.

The advantages of chromatography are that molecules can be separated on a large scale, relatively rapidly. Disadvantages include loss of materials by non-specific adsorption, uneven packing and particle shifting (void formation and channeling) of the chromatographic material, multiple chromatographies required for complete separation, and large sample sizes.

Electrophoresis is another widely used separation technique in the biologically-related sciences. There are three main ways of using electrophoresis: standard continuous zone electrophoresis, isoelectric focusing, and isotachophoresis. Molecules such as peptides, proteins, and oligonucleotides can be separated by causing them to migrate in a buffer solution under the influence of an electric field. Often the separation medium is a gel such as agarose or polyacrylamide to minimize convective mixing.

In electrophoresis, molecules are primarily separated by different electrophoretic mobilities caused by their different molecular size and/or charge. Other variables affecting separation include the deformabilities and shapes of the macromolecular species. Separations by charge are generally limited to lower molecular weight molecules since the effective charges on a per-mass basis of the larger molecules, such as nucleotides in excess of 1,000 bases, do not differ sufficiently with length. Surfactants such as sodium dodecyl sulphate (SDS), can be used to neutralize the effect of charge differences of most proteins and peptides, so that separation is primarily a function of molecular size, as when proteins are separated by polyacrylamide gel electrophoresis in the presence of SDS (SDS-PAGE). Separations on the basis of charge, irrespective of molecular weight, can also be achieved based on the isoelectric points of the molecules, using a pH gradient, as in isoelectric focusing (IEF).

Early techniques involved imposing an electric field across a slab of gel and placing a sample of material to be analyzed on one end of the gel. Most electrophoretic separations now use commercially available gel columns or slab gel apparatus, distributed, for example, from Pharmacia and Bio-Rad Laboratories. Typically, a monomer solution, one or more crosslinking agents, and surfactants are added to the apparatus and polymerization initiated. An aqueous buffer is usually included to provide an electrically conductive medium in the gel. Apparatus are available both for analytical and for large scale preparative separations.

Recently, microcapillary tubes have been developed for use in microcapillary gel electrophoresis (high-performance capillary electrophoresis, HPCE). These tubes, generally formed of fused silica with an outer polyimide coating, wall thickness in the range of 25 to 40 microns and inner diameter in the range of 25 to 100 microns, are filled with a polyacrylamide gel, the ends placed in an appropriate buffer, and an electric field applied to the gel. The advantage of the HPCE is that the heat resulting from the applied electrical field is efficiently removed due to the high surface area, so a higher current can be applied, thereby decreasing the time required to achieve the desired separation.

All of these methods are still limited as to the separations that can be achieved, particularly of nucleotides and molecules having very similar molecular sizes and charges.

It is therefore an object of the present invention to provide innovative methods and compositions for separation of molecules, particular of molecules that are difficult to separate with existing technology.

It is a further object of the present invention to provide methods and compositions that can be used with existing gel chromatographic and electrophoretic equipment.

It is a still further object of the present invention to provide methods and compositions to separate molecules on both analytical and preparative scales.

SUMMARY OF THE INVENTION

A method and compositions for separating molecules based on molecular weight, shape, size, charge, hydrophilicity/hydrophobicity, hydrogen bonding, chirality, and/or even molecule-specific binding affinity using a mosaic matrix formed by polymerizing a dispersion of microdomains (islands) or dispersoids within a continuous polymeric matrix. The dispersoids and matrix can be of the same or different hydrophobicity or hydrophilicity. The dispersoids can be porous or non-porous (pellicular). The "dispersed phase" may also be continuous, so that the major and minor phase are co-continuous like intertwining, interlocking matrices. Both phases may be polymerized at the same time or one phase, the dispersed phase, pre-formed and distributed in a pre-gel mixture, the continuous phase, which is then polymerized to trap the dispersoids.

The mosaic matrix can be used with existing chromatographic and electrophoresis apparatus to effect an enhanced separation of molecules, particularly of nucleic acids, by application of a solution and/or an electrical field simultaneously or separately to the matrix. The solution can form a pH or ionic gradient, and be applied using gravity or under pressure. The electrical field can be continuous, pulsed, or two-dimensional.

In the preferred embodiment, both dispersoids and matrix are formed by precisely controlled crosslinking of monomers and have a uniform density and pore size, although the continuous phase may form a composition gradient, or contain mixtures of dispersoids. Preferably, one of the dispersoids and matrix is hydrophobic and the other is hydrophilic. Dispersoids can be prepared by either emulsion or suspension polymerization, depending on the size preference, with the latter used for spheres more than one micron in diameter. In the most preferred embodiment, the mosaic matrix is polymerized in the chromatographic or electrophoretic apparatus using a method minimizing shrinkage, void formation, and internal stress.

BRIEF DESCRIPTION OF THE DRAWINGS

FIG. 1A is representative of the embodiment having dispersoids distributed within a continuous matrix and FIG. 1B is representative of the embodiment having a co-continuous morphology.

DETAILED DESCRIPTION OF THE INVENTION

Figure 1A:
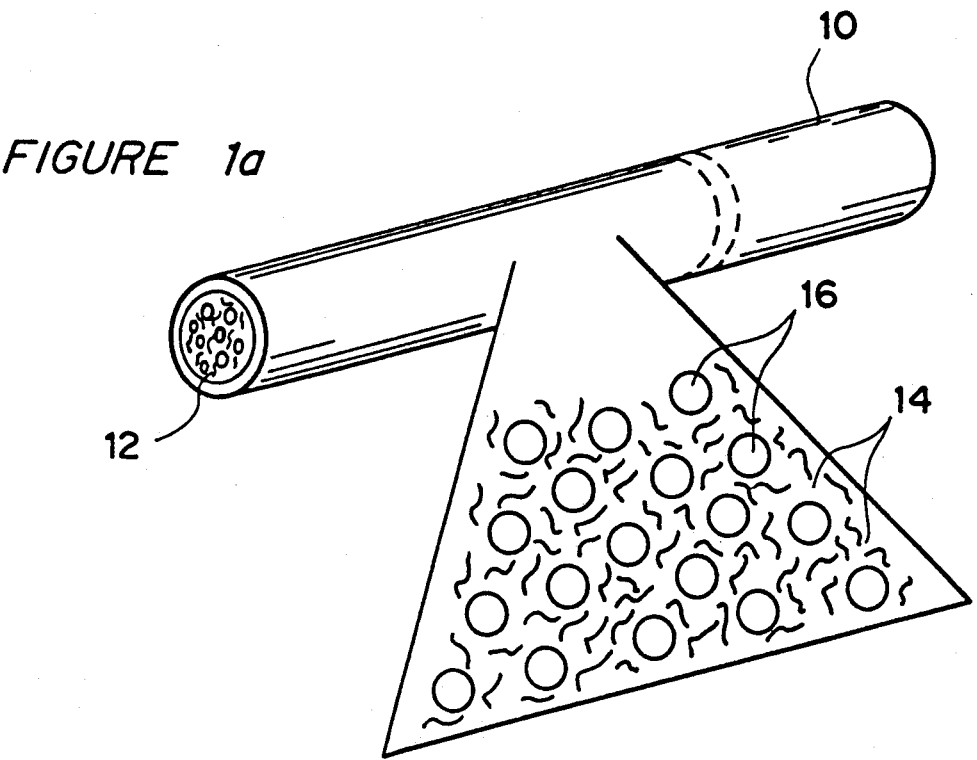
FIG. 1A and 1B is an expanded cross-sectional view of a mosaic matrix according to the present invention in a gel electrophoresis tube, where

The mosaic matrix is characterized by tremendous flexibility and adaptability to a variety of simultaneous (combined) or individual (separate) chromatographic and electrophoretic separations. The general requirements are described in detail below, then in relation to known methods for chromatographic and electrophoretic separations. These are not intended to be limiting, since additional methods and apparatus can be utilized.

Preparation of the mosaic matrix

Preformed Dispersoids

Spheres or particulates (referred to herein jointly as spheres or "dispersoids", unless otherwise noted) can be purchased commercially from a variety of sources or prepared using methods known to those skilled in the art, such as conventional emulsion or suspension polymerization, depending on size preference, with the latter method being preferred for formation of spheres in excess of one micron in diameter.

Microdomains or dispersed phases

Microdomains (referred to herein jointly with spheres or particulates as "dispersoids" unless otherwise noted) are formed by co-polymerizing a second, immiscible polymer solution within the gel matrix, as described below. These can be twisting and turning long "cylindrical" shapes that are interconnected to form a co-continuous phase.

Composition

Crosslinked or uncrosslinked spheres, particles, or "dispersoids" of any hydrophilic or hydrophobic polymer or copolymer can be used, as well as inorganic materials such as silica and glass. Examples of polymeric materials that are suitable include natural polymers such as polysaccharide, dextran, cellulose, alginate, and agarose. Synthetic polymers that are useful include polyacrylamide, poly(acrylic acid), poly(methacrylic acid) and methyl, ethyl, propyl, and butyl derivatives thereof, polystyrene and sulfonated derivatives thereof, amino-substituted polystyrenes, poly(4-hydroxy styrene), poly(vinyl alcohol), poly(ethylene oxide), polycarbonates, polyester, polyethylene, polypropylene, polybutylene, polyisobutylene, polyamides (such as nylon), poly(ethylene glycol), hydroxylated cellulose derivatives, poly(vinyl acetate), polymethacrylate and methyl, ethyl, propyl, and butyl derivatives thereof, styrene-divinylbenzene, acrylamide-bisacrylamide, epoxy, polysulfone, polyethyleneterephthalate, urethanes, mono- and di-substituted vinyls, teflon, silicone and copolymers thereof.

The dispersoids can be used alone or in combination with other molecules or reagents bound to the dispersoids to enhance or alter separation. For example, antigen, antibody, lectin, or receptor molecules may be bound to the dispersoids which selectively interact with some molecules in the mixture to be separated. The dispersoid itself may have binding properties, such as chelating or metal binding properties. This interaction can be modified by altering the pH or ionic strength of the gel buffer, or the applied electrical field.

Size and porosity

These materials can be formed into appropriate shapes for use in the mosaic matrix using known technology. Choice of porosity depends n the sample molecular size range to be resolved. Porosity can range from negligible, where the molecules to be separated will not penetrate the spheres, to microns, where most of the molecules to be separated pass into the pores of the spheres, delaying their migration through the mosaic matrix. Examples of non-porous material are dense silica and tightly crosslinked polymer or crystalline polymer. Examples of porous materials are porous glass (silica) and hydrated crosslinked polymers, with porosity determined by the degree of crosslinking.

The size of the dispersoids varies depending on the application. They can range from less than one micron (as small as a few hundred Angstroms if block copolymers or graft copolymers are used) to hundreds of microns in diameter. The smaller the domain size, the larger the interfacial area. As a result, surface interactions such as chromatographic adsorption becomes important in the separation. Larger domains give a smaller surface area on a per-total-domain-fraction-basis.

Hydrogen bonding capability

The dispersoids can be hydrophobic or hydrophilic. They can be the same as the gel matrix, of a greater or less degree of hydrophobicity or hydrophilicity, or hydrophobic when the matrix is hydrophilic or vice versa. In general, the hydrophobic materials will locally enhance the electrical field between adjacent domains, spatially accelerating and retarding polyelectrolytes in a manner similar to a pulsed electrical field.

Gel matrix

Composition and polymerization

Generally any monomer or monomer mixture, in combination with an initiator and/or catalyst to activate the monomer to cause chain lengthening, either by step process or addition, can be used to form the matrix. The initiator can be a compound or agent which breaks the double bonds or activates the functional groups of the monomer. For example, free-radical initiation can be caused by either thermal or UV-induced decomposition initiator.

The polymers are polymerized using known methodology from monomers such as acrylic acid, acrylamide, methyl, ethyl, propyl, and butyl derivatives thereof, cellulose and hydroxylated derivatives thereof, vinyl alcohol, vinyl acetate, ethylene oxide, ethylene glycol, and styrene, and other polymers and copolymers as listed above in relation to the dispersoid composition. For separation of biomolecules using gel electrophoresis, aqueous soluble vinyl monomers are particularly useful. Examples including acrylic acid, acrylamide, methacrylic acid, vinyl alcohol, vinyl acetate, methacrylamide, 2-oxazolines, and pyrrolidone derivatives such as vinyl or methyl pyrrolidone. Some non-aqueous soluble monomers are styrene, methyl methacrylate, and silanes. For the water soluble monomers, a typical concentration is in the range of 3 to 20% w/v.

Hydrogen bonding capability

As described with respect to the dispersoids to be incorporated into the matrix, the matrix itself can be designed to have a specific hydrogen binding capability, thereby affecting not only the passage of hydrophobic or hydrophilic molecules through the matrix, but also altering the effective electrical field passing through the matrix. Sometimes, mere surface (interfacial) interactions suffice, especially in the case of pellicular packing (domains). Since such non-porous packing does not allow penetration of the sample molecules, the separation principles based on diffusion into the dispersoid, or particle, interior are not operative.

Polymerization of dispersoids within gel matrix

The gel content (%T) and degree of crosslinking (%C) are both dictated by the size range of the species to be separated. Typically, the matrix will be crosslinked to between one and ten percent. A typical loading level for the dispersoid (or "domains") within the matrix can be as high as 50% weight to volume (w/v).

In general, a broad temperature range can be used for polymerization, as long as the solvent, or water in which the monomer is dissolved, does not boil or freeze. The conditions and reagents will determine the time of polymerization, which should not be too slow so that the production yield throughput is reasonable.

In general, the basic structure of the gel is determined by the monomer. A comonomer or crosslinker is usually used to change the basic structure of the gel, depending on the nature of the molecules to be separated. For polyacrylamide gels, wellknown crosslinking agents are N,N'-bisacrylylcystamine (BAC), N,N'-diallyltartardiamine (DATD), N,N'-(1,2-dihydroxyethylene) bisacrylamide (DHEBA), ethylene diacrylate (EDA), and others. For all of these crosslinkers, a typical range of concentrations is from 2 to 5% weight/total solid weight. Those skilled in the art will understand that other concentrations may be used depending on the desired structure and the nature of the separation to be performed.

Other initiators may also be used, provided they are appropriate for the monomer/crosslinker combination. For the above combinations, for example, potassium persulfate may be substituted for ammonium persulfate as an initiator. In general, however, the classes of compounds that are useful as thermal decomposition initiators for general polymerization reactions are somewhat limited and other classes that are typically used are those with O—O, S—S, or N—O bonds, since these classes of compounds exhibit bond dissociation energies in the range of 100-170 kJ/mole. Compounds with higher or lower bond dissociation energies will typically dissociate too slowly or too rapidly. A notable exception to this general rule are some azo compounds, such as 2,2'=Azobisisobutyronitrile (AIBN), which has a dissociation energy of about 290 kJ/mole, but the driving force for homolysis there is the formation of the highly stable nitrogen molecule. It is expected that these compounds would behave similarly when used for polymer gel formation for separation purposes. For the more general polymer systems where thermally initiated polymerization is used, the peroxides have typically been the initiator of choice (eg. acyl peroxides such as acetyl and benzoyl peroxides, alkyl peroxides such as cumyl and t-butyl peroxides, hydro-peroxides such as t-butyl and cumyl hydro-peroxides, and peresters such as t-butyl perbenzoate). Similarly, other accelerators may be used as catalysts for the polymerization and crosslinking, particularly those that will cause the gelation reaction to become a stronger function of temperature. The use of crosslinkers tends to make the gel much more stable during use as well as contributing to the establishment of an effective pore size for the gel.

Surface modifiers can be added to the gel to change the nature of the interaction of the molecules with water, with each other, and with their environment, since these molecules are often amphoteric and tend to stick together in aqueous solutions to form micelles. Examples of surface modifiers are urea and surfactants. Urea weakens intramolecular hydrogen bonding, which helps to ensure denaturation of any protein solutes injected into the capillary. Another useful modifier is guanidine, typically about 5 M, which is sometimes used in combination with urea. A broad range of detergent-like molecules serve well as surfactants, such as Triton-x™, Tween-x™, and Brij-x™. These will frequently form a sheath-like coating over the species to be separated. The surfactants thereby help separate the solute into individual molecules which can then migrate in an isolated fashion down the gel.

Buffering agents may also be used for pH stabilization or control of ionic strength, since some molecules tend to bind to particular ions. Examples of other buffers include borates, phosphates, citrates, and carbonates. Still other useful modifiers include alcohol and acetonitrile.

Additional modifying agents may also be used which generally depend on the type of molecule being analyzed, and on how the interaction of the solute with the other compounds in the gel matrix is to be altered. Dispersoids may be laced (doped) or have immobilized antigen or antibody, or other specific binding molecules such as a lectin or receptor. Either phase may be chiral, or both may be for resolution of racemic mixtures. Those skilled in the art will appreciate that there are many other useful modifiers which can be used to control or change the nature of the separation process.

Since dispersoids ("preformed microdomains") are generally of colloidal size, they undergo spontaneous Brownian diffusion, and automatically form a suspension. When aided by minor stirring, a uniform dispersion can be prepared for matrix gelation. Also, since the microdomains are almost neutrally buoyant in the matrix, they can easily be suspended indefinitely until the matrix is gelled. A surfactant such as SDS can also be used to stabilize the dispersion.

Alternatively, microdomains are formed by polymerizing both the continuous gel matrix and a dispersed phase (or cocontinuous phase) formed from a monomer-crosslinking solution that is immiscible with the continuous gel matrix.

Wall coupling agents

The use of a wall coupling agent has been found to significantly enhance the stability of the gels produced, since the gels are then held firmly in place by the wall. Use of such wall couplings is a common practice in the art. In a preferred embodiment, prior to filling the apparatus with the monomer in combination with other crosslinking reagents and dispersoids, 3-methacryloxy-propyl-trimethoxysilane (MAPTMS) in acetone is used to coat the apparatus. The apparatus is then air dried and heated in an oven for three hours at about 130° C. to effect MAPTMS binding to the capillary wall surfaces. The MAPTMS promotes strong wall adhesion and a dense, highly cross-linked gel adjacent to the wall. Other wall coupling agents and procedures may also be used. For example, another approach is to covalently bond aminopropyltrimethoxysilane or aminopropyltriethoxysilane to the wall. N-acryloxysuccimide is then used to cause substitution addition. This is then followed by treatment with diethylacrylamide to cause crosslinking of the materials on the wall. In all of the procedures above, the goal is to leave a wall surface covered with double bonds directly linked to the wall by chemical bonds. These double bonds can then react with acrylamide monomers and crosslinkers.

Methods of using the mosaic matrix

General references for separations, both analytical and preparative, are *Analytical Biotechnology* Csaba Horvath and John Nikelly, editors, *ACS Symposium Series* volume 434 (1990), and "Protein Purification" Ladisch, Willson, Painton, and Buidler, editors, *ACS Symposium Series* volume 43 (1990), the teachings of which are incorporated herein.

Gel permeation chromatography

Gel permeation chromatography (GPC), also known as gel filtration chromatography (GFC) or size exclusion chromatography (sec), separates molecules based on molecular weight sieving. In the general situation, porous polymeric spheres are packed by settling into an appropriate column and buffer is pumped from one end of the column to the other. The smaller molecular weight molecules will elute last, being delayed by passage through the porous spheres. The size exclusion of the molecules is determined by the degree of crosslinking of the spheres.

In the method described herein, size exclusion chromatography can be achieved in a column containing only one continuous matrix firmly tethered to the wall, a distinct advantage over the prior art multiple column methods.

High pressure liquid chromatography

High pressure liquid chromatography (HPLC) has now been adapted for use on a small scale, termed microcolumn HPLC. This uses fused silica columns having a diameter of approximately one hundred microns that are packed with three to five micron porous silica particles, having a frit or filter at one end to retain the silica particles. The mosaic matrix, incorporating silica or polymeric dispersoids into a polymeric matrix, is particularly advantageous for use with this process because the matrix prevents compaction and shifting of the dispersoids under the high pressure liquids used to effect the separations. The techniques described above can be adapted for crosslinking of the matrix to the column walls, thereby minimizing voids and channeling which decrease resolution of separated molecules.

Batch separation chromatograph

Molecules are routinely separated by interaction with cationic, anionic, hydrophobic or hydrophilic matrices, where differential binding is achieved by controlling the pH and/or ionic strength of the application and elution buffers. Separations are also achieved by binding of molecules within the mixture to be separated to molecules, for example antibodies and lectins, that are bound to the separation media. Molecules of different chirality can also be separated in this manner.

In both gel permeation chromatography and batch separation chromatography, the mosaic matrix can be substituted for the conventional matrices, in whole or in part. Higher flow rates are achieved because the matrix prevents compaction of the separations media, and molecules not normally separated by molecular weight or charge alone can be separated based on both properties simultaneously.

Slab or column gel electrophoresis

As described by Maniatis, et al., *Molecular Cloning: A Laboratory Manual* (Cold Spring Harbor Laboratory, N.Y. 1982), the teachings of which are incorporated herein, polyacrylamide gel electrophoresis is used to analyze and prepare fragments of DNA of less than 1,000 nucleotide bases in length. The gels can be cast in a variety of polyacrylamide concentrations, ranging from 3.5% to 20%, depending on the sizes of the fragments of interest. Generally, the percent acrylamide to effective range of separation is: 3.5%–100 to 1000 nucleotides; 5.0%–80 to 500 nucleotides; 8.0–60 to 400; 12.0–40 to 200; and 20.0–10 to 100.

Polyacrylamide gels are almost always poured between two glass plates that are held apart by spacers. Gels can range in length from 10 cm to 100 cm, depending on the separation required. They are run in either the vertical or horizontal position.

A typical recipe for a 3.5% gel is 11.6 mls of 30% acrylamide (29 g acrylamide, 1 g N,N'-methylene bisacrylamide, water added to 100 ml); 76.3 ml water; 2.1 ml 3% ammonium persulfate (0.3 g ammonium persulfate plus water to 10 ml); 10.0 ml 10× Tris-borate buffer (0.89 M Tris-borate, 0.89 M boric acid, 0.02 M EDTA). Gels are electrophoresed at between 1 V/cm and 8 V/cm in 1× Tris-borate buffer.

As also described by Maniatis, et al., agarose gel electrophoresis is also used to separate, identify, and purify DNA fragments. As little as 1 ng of DNA can be detected by direct examination of the gel in ultraviolet light. The percent agarose is correlated with the size of fragments to be separated. In general, 0.3% agarose for 5,000 to 60,000 bases; 0.6% for 1,000 to 20,000 bases; 0.7% for 800 to 10,000 bases; 0.9% for 500 to 7,000 bases; 1.2% for 400 to 6,000 bases; 1.5% for 200 to 4,000 bases; and 2.0% for 100 to 3,000 bases. It is apparent from a comparison with the numbers for the acrylamide gels that the agarose gels are used for separation of longer DNA sequences than the acrylamide gels. Agarose gels are generally run at room temperature, at no more than 5 V/cm, usually in a Tris-acetate, borate or phosphate buffer at about 50 mM and pH between 7.5 and 7.8. The amount of DNA applied to the gel ranges from between 0.2 and 0.5 μg and 5 to 10 μg/slot.

Ultrathin gels are used in place of the conventional slab gels to increase heat dissipation and thereby allow the use of higher voltages, resulting in shorter running times. The use of the differential gelling process described in co-pending application U.S. Ser. No. 07/345,715 entitled "Gel Casting Method and Apparatus" filed May 1, 1989 by David S. Soane, and the method for making gradient gels described in co-pending application U.S. Ser. No. 07/345,616 entitled "Casting of Gradient Gels" filed May 1, 1989 by David S. Soane, the teachings of which are incorporated herein.

These procedures are adapted for use with the mosaic matrix by dispersing into either the acrylamide or agarose the polymeric dispersoids, then polymerizing or solidifying the gel, as described above.

The mixture of molecules to be separated are applied to the gel, and an electrical current applied. A solvent flux can also be applied to the gel, either in the same co-linear direction (working additively), opposite direction (working against each other), or perpendicular direction to the direction of the electric field. The electric field can be continuous, pulsed, two dimensional, or varied to effect the desired separation. For example, in a unique application of the mosaic matrix, the voltage is ramped gradually up to sequentially release molecules bound to the dispersoids. The released molecules are then sequentially eluted from the gel using the applied solvent flux and/or the applied electrical field. The solvent composition can remain the same over time (static electric field and isocratic solvent) or change with time (ramping electric field and solvent gradient).

Microcapillary gel electrophoresis

Microcapillary gel electrophoresis, also known as open tubular free-zone electrophoresis and isotachophoresis, described, for example, in U.S. Pat. No. 4,865,707 to Karger, et al., has been developed in place of more conventional slab gel electrophoresis to increase heat dissipation by increasing surface area, thereby decreasing the electrophoresis time, and to increase the resolution of materials separated from mixtures. In the conventional process, resolution between compounds is influenced by sample size, ionic materials in the samples, and the gel concentration, as well as applied field and the electrical current employed.

As described herein, the mosaic matrix can be substituted for the more conventional acrylamide gel matrix in the microcapillaries to achieve even greater resolution. The capillaries are formed of fused silica or glass, and preferably coated on the outside with a polyimide. Bore diameters range from 10 microns to 1000 microns, although plastic capillaries (e.g., teflon) could be used as well.

An example of a mixture that can be used is:

A. Gel Matrix (1) Monomer: Acrylamide (10% w/v, 10 gms/100 ml)
(2) Comonomer/Crosslinker: N,N'-methylenebisacrylamide (Bis, 3% w/total solid weight)
(3) Initiator: Ammonium persulfate (0.05% w/v)
(4) Coinitiator/Accelerator: N,N,N'-tetramethylethylene-diamine (TEMED, 0.06% v/v, i.e. 0.0006 ml/ml)
(5) Surfactant: Sodium dodecylsulfate (SDS, 0.1% w/v)
(6) Buffer: Tris/Phosphate (0.1 M)
(7) Modifier: Urea (7 M)

B. Dispersoids or "microdomains"

(1) Spheres of approximately 0.5 micron diameter of Sephadex TM, Sepharose TM, (both available from Pharmacia), dextran, polyamide (e.g., synthetic peptides), poly(ethylene glycol) (PEG), nylon, poly(ethylene oxide) (PEO), poly(vinyl alcohol), hydroxyethylcellulose (HEC), hydroxyethylmethacylate (HEMA), or (2) "microdomains", of pellicular hydrophobic materials such as styrene and polyethylene, formed by the addition of an immiscible monomer-crosslinker solution to the monomer-crosslinker solution forming the gel matrix, alone or in combination with a surfactant to maintain a stable emulsion.

Figure 1B:
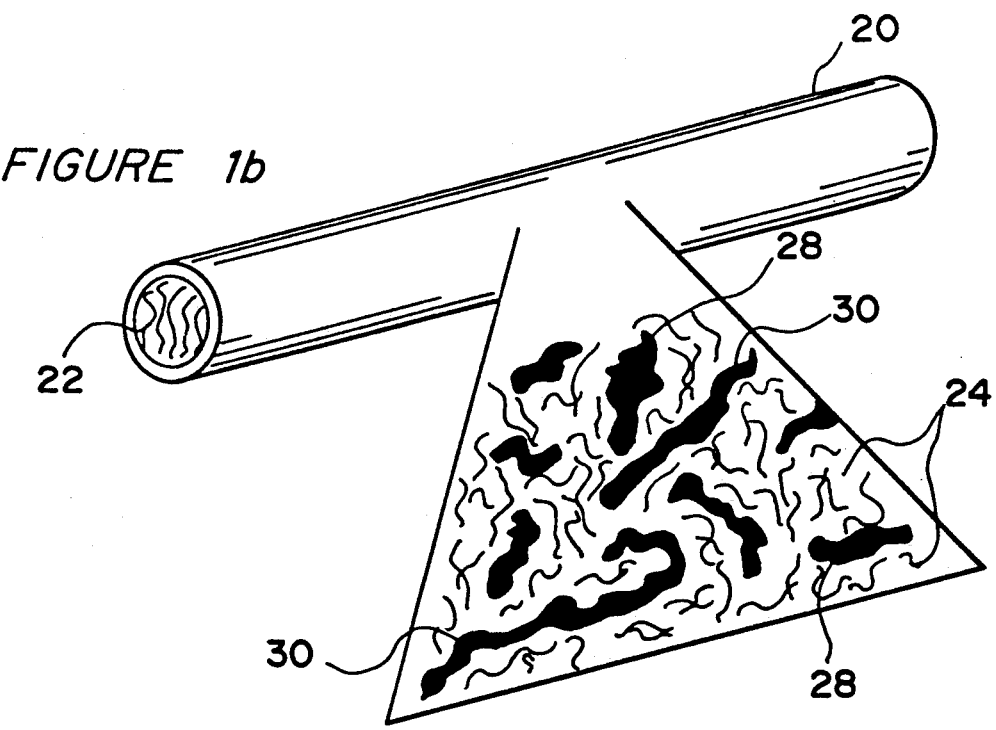

FIG. 1A is a view of capillary tubing 10 which has been filled with a liquid mixture 12 of materials forming a gel 14 and polymeric spheres 16. FIG. 1B is a view of capillary tubing 20 which has been filled with a liquid mixture 22 of materials forming a gel 24 and microdomains 26, areas that are not miscible with the gel material, and can form either discrete regions 28 or interconnected tortuous paths for the molecules to be separated 30.

The mixture is preferably polymerized sequentially, by pulling the capillary tube through a heated (or irradiated) region, beginning at one end and proceeding uniformly as a function of the crosslinking to the other end of the capillary, as described in co-pending application U.S. Ser. No. 07/345,715 entitled "Gel Casting Method and Apparatus" filed May 1, 1989 by David S. Soane. For a 100 micron fused silica capillary, a pulling rate of 0.8 cm/min was used with a heated zone temperature of 43° C. and a 5 cm (2 in) heated zone length.

In both the microcapillary gel electrophoresis and the microcolumn HPLC, the loading and polymerization process using the mosaic matrix is considerably quicker than the overnight packing now required, and decreases the chance of scratching of the column interior wall. The mosaic matrix is also advantageous because the matrix can be used to achieve a greater separation than otherwise achievable, by interacting with the molecules by charge or by sieving the molecules, where the crosslinking of the matrix is between one and ten percent. Alternatively, the porosity of the matrix can be increased (by using less than one percent crosslinking) to increase the flow rate through the column to a level greater than that possible using the packed silica particles. Also, the capillaries can be loaded with different matrix quantities than can be achieved with the particle loading with the method currently in use.

Multi-stage columns or slab gels

Mosaic matrices of different compositions can be combined to effect different separations in the same apparatus, either as a "gradient" of size, charge, hydrophobicity, etc., or in discrete units equivalent to more than one gel tube or slab juxtaposed. This can be used to achieved the same effect as multiple electrophoreses or elutions.

The mosaic matrix can also be used on either an analytical or preparative scale.

Modifications and variations of the methods and compositions of the present invention will be obvious to those skilled in the art from the foregoing detailed description. Such modifications and variations are intended to come within the scope of the appended claims.

I claim:

1. A composition for use in chromatographic and electrophoretic separations of molecules comprising
    dispersoids,
    a solution immiscible with the dispersoids containing chemical monomers which, in the presence of crosslinking agent and initiator, polymerize to form a continuous polymeric matrix incorporating the dispersoids, wherein the separation properties of the dispersoids are different from the separation properties of the polymeric matrix,
    a crosslinking agent and initiator.

2. The composition of claim 1 wherein the monomers have been polymerized to form a solid matrix containing the dispersoids within the matrix.

3. The composition of claim 2 wherein the polymeric matrix and the dispersoids have different chemical properties, the chemical properties being selected from the group consisting of hydrophilicity, hydrophobicity, hydrogen bonding, chirality, and binding affinity for specific molecules.

4. The composition of claim 2 further comprising a solid support.

5. The composition of claim 4 wherein the solid support is selected from the group consisting of tubes, slabs, microcapillaries, and columns for use in electrophoresis and gel chromatography.

6. The composition of claim 1 wherein the dispersoids are solid particulates formed prior to polymerization of the matrix.

7. The composition of claim 1 wherein the dispersoids are polymerized from a monomer solution immiscible with the monomer solution forming the polymeric matrix, wherein the dispersoids form a second, co-continuous phase within the polymeric matrix.

8. The composition of claim 1 wherein the dispersoids are selected from the group consisting of porous and non-porous materials.

9. The composition of claim 1 wherein the dispersoids are of different mass.

10. The composition of claim 1 wherein the dispersoids are formed of a compound selected from the group consisting of silica, glass, polysaccharide, dextran, cellulose, alginate, and agarose, polyacrylamide, poly(acrylic acid), poly(methacrylic acid) and methyl, ethyl, propyl, and butyl derivatives thereof, polystyrene and sulfonated derivatives thereof, amino-substituted polystyrenes, poly(4-hydroxy styrene), poly(vinyl alcohol), poly(ethylene oxide), polycarbonates, polyester, polyethylene, polypropylene, polybutylene, polyisobutylene, polyamides, poly(ethylene glycol), hydroxylated cellulose derivatives, poly(vinyl acetate), polymethacrylate and methyl, ethyl, propyl, and butyl derivatives thereof, styrene-divinylbenzene, acrylamide-bisacrylamide, epoxy, polysulfone, polyethyleneterephthalate, urethanes, mono- and di-substituted vinyls, urethanes, mono- and di-substituted vinyls, teflon, silicone and copolymers thereof.

11. The composition of claim 1 wherein the monomers form polymers selected from the group consisting of polysaccharide, dextran, cellulose, alginate, agarose, polyacrylamide, poly(acrylic acid), poly(methacrylic acid) and methyl, ethyl, propyl, and butyl derivatives thereof, polystyrene and sulfonated derivatives thereof, amino-substituted polystyrenes, poly(4-hydroxy styrene), poly(vinyl alcohol), poly(ethylene oxide), polycarbonates, polyester, polyethylene, polypropylene, polybutylene, polyisobutylene, polyamides (such as nylon), poly(ethylene glycol), hydroxylate cellulose derivatives, poly(vinyl acetate), polymethacrylate and methyl, ethyl, propyl, and butyl derivatives thereof, styrene-divinylbenzene, acrylamide-bisacrylamide, epoxy, polysulfone, polyethyleneterephthalate, urethanes, mono- and di-substituted vinyls, urethanes, mono- and di-substituted vinyls, teflon, and copolymers thereof.

12. A method for providing a composition for separation of molecules comprising
    mixing dispersoids,
    a solution immiscible with the dispersoids containing chemical monomers which, in the presence of crosslinking agent and initiator, polymerize to form a continuous polymeric matrix incorporating the dispersoids, wherein the separation properties of the dispersoids are different from the separation properties of the polymeric matrix,
    crosslinking agent and initiator,
    and polymerizing the monomers to form a continuous matrix containing the dispersoids within the matrix.

13. The method of claim 12 wherein the dispersoids are solid particulates formed prior to polymerization of the matrix.

14. The method of claim 12 wherein the dispersoids are polymerized from a monomer solution immiscible with the monomer solution forming the polymeric matrix after initiation of polymerization of the monomer solution forming the polymeric matrix.

15. The method of claim 12 wherein the polymeric matrix and the dispersoids have different chemical properties, the chemical properties being selected from the group consisting of hydrophilicity, hydrophobicity, hydrogen bonding, chirality, and binding affinity for specific molecules.

16. The method of claim 12 wherein the dispersoids are selected from the group consisting of porous and non-porous materials.

17. The method of claim 12 wherein the dispersoids are of different mass.

18. The method of claim 12 wherein the dispersoids are formed of a compound selected from the group consisting of silica, glass, polysaccharide, dextran, cellulose, alginate, and agarose, polyacrylamide, poly(acrylic acid), poly(methacrylic acid) and methyl, ethyl, propyl, and butyl derivatives thereof, polystyrene and sulfonated derivatives thereof, amino-substituted polystyrenes, poly(4-hydroxy styrene), poly(vinyl alcohol), poly(ethylene oxide), polycarbonates, polyester, polyethylene, polypropylene, polybutylene, polyisobutylene, polyamides, poly(ethylene glycol), hydroxylated cellulose derivatives, poly(vinyl acetate), polymethacrylate and methyl, ethyl, propyl, and butyl derivatives thereof, styrene-divinylbenzene, acrylamide-bisacrylamide, epoxy, polysulfone, polyethyleneterephthalate, urethanes, mono- and di-substituted vinyls, urethanes, mono- and di-substituted vinyls, teflon, silicone and copolymers thereof.

19. The method claim 12 wherein the monomers form polymers selected from the group consisting of polysaccharide, dextran, cellulose, alginate, agarose, polyacrylamide, poly(acrylic acid), poly(methacrylic acid) and methyl, ethyl, propyl, and butyl derivatives thereof, polystyrene and sulfonated derivatives thereof, aminosubstituted polystyrenes, poly(4-hydroxy styrene), poly(vinyl alcohol), poly(ethylene oxide), polycarbonates, polyester, polyethylene, polypropylene, polybutylene, polyisobutylene, polyamides (such as nylon), poly(ethylene glycol), hydroxylated cellulose derivatives, poly(vinyl acetate), polymethacrylate and methyl, ethyl propyl, and butyl derivatives thereof, styrene-divinylbenzene, acrylamide-bisacrylamide, epoxy, polysulfone, polyethyleneterephthalate, urethanes, mono- and di-substituted vinyls, teflon, and copolymers thereof.

20. The method of claim 12 wherein the monomers are crosslinked to form a gradient of pore size through the polymeric matrix.

21. The method of claim 12 wherein the matrix is polymerized in a slab gel electrophoresis apparatus.

22. The method of claim 12 wherein the matrix is polymerized in a microcapillary.

23. The method of claim 12 wherein the matrix is polymerized in a gel chromatography column.

24. The method of claim 12 further comprising providing a solution containing a mixture of molecules to be separated to the polymeric matrix.

25. The method of claim 24 wherein the gradient is a pH gradient.

26. The method of claim 24 wherein the gradient is an ionic gradient.

27. The method of claim 24 wherein the gradient is a co-solvent composition gradient.

28. The method of claim 24 further comprising applying an electric field to the polymeric matrix to effect a separation of the molecules within the matrix.

29. The method of claim 28 wherein molecules in the mixture bind to the dispersoids and the electric field is ramped up with time to sequentially interrupt the binding of different molecules to the dispersoids, thereby effecting a separation of the molecules.

30. The method of claim 28 further comprising simultaneously applying an electrical field and solvent flux to the mosaic matrix to effect a separation of the molecules.

31. The method of claim 30 wherein the direction of the solvent flux is perpendicular to the direction of the electric field.

32. The method of claim 30 wherein the direction of the solvent flux is opposite to the direction of the electric field.

33. The method of claim 24 further comprising applying a solution to the polymeric matrix, the solution forming a gradient as it moves through the matrix.

* * * * *